United States Patent [19]

McCall

[11] 4,450,846

[45] May 29, 1984

[54] ELECTRICAL PULSE ACUPRESSURE APPARATUS AND METHOD OF MAKING SAME

[76] Inventor: Francis J. McCall, 19231 Victory Blvd., Reseda, Calif. 91335

[21] Appl. No.: 334,317

[22] Filed: Dec. 24, 1981

[51] Int. Cl.$^3$ ............................................. A61N 1/02
[52] U.S. Cl. ..................................... 128/789; 128/907
[58] Field of Search .................... 128/303.13, 789, 783, 128/784, 791–793, 799, 802, 803, 907, 735, 329 A

[56] References Cited

U.S. PATENT DOCUMENTS

| | | | |
|---|---|---|---|
| 1,623,552 | 4/1927 | Pollard | 128/789 |
| 3,900,020 | 8/1975 | Lock | 128/735 |
| 4,037,590 | 7/1977 | Dohring et al. | 128/303.13 X |

*Primary Examiner*—Lee S. Cohen
*Attorney, Agent, or Firm*—Jack C. Munro

[57] ABSTRACT

An electrical pulse acupressure apparatus adapted to be worn by a human being within the ear. The apparatus includes an applicator in the form of a housing which is specially, exteriorly configurated to conform in a tight fitting manner within the interior of the ear. Exteriorly embedded within the applicator are a plurality of metallic nodules which have been set a prescribed locations to connect with known acupuncture points located within the ear. Each of the metallic nodules connects with a chamber formed internally within the applicator. Within the chamber is located a hardened electrically conductive paste. An electrical connector is embedded within the paste. A plug is to removably connect with the electrical connector. The plug includes an auxiliary electrical connection. The auxiliary electrical connection is to connect with a second acupressure apparatus. The method includes inserting the paste in liquid form within the chamber of the applicator and embedding the electrical connector within the paste and then permitting such to harden. The plug is to be connected to an electrical pulse generator to transmit electrical pulses which are to be conducted through the hardened paste to the metallic nodules.

3 Claims, 6 Drawing Figures

U.S. Patent            May 29, 1984            4,450,846
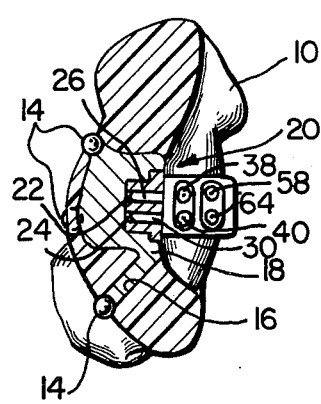
𝕱𝖎𝖌.2.
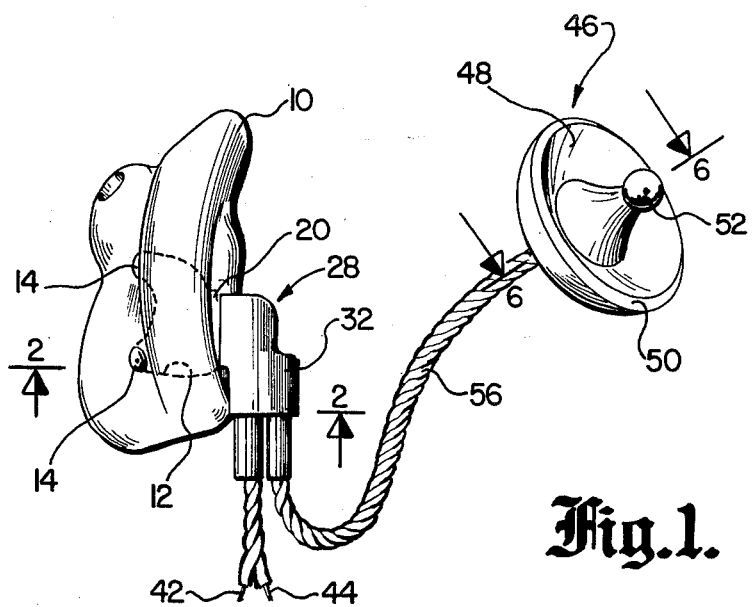
𝕱𝖎𝖌.1.
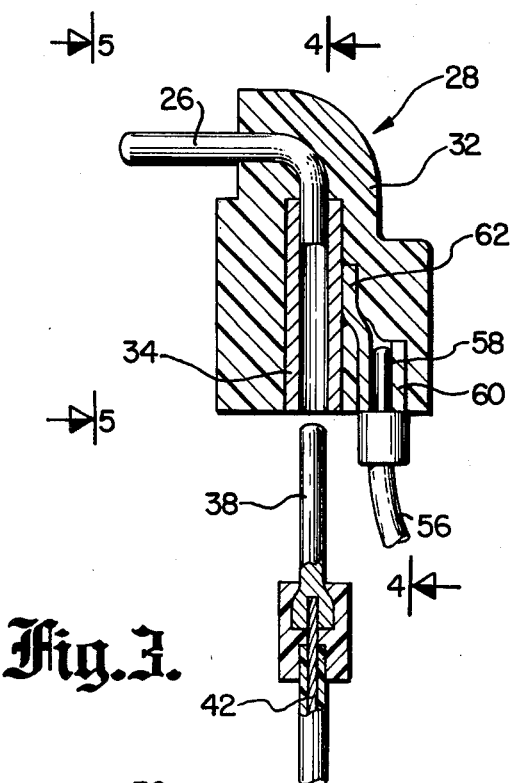
𝕱𝖎𝖌.3.
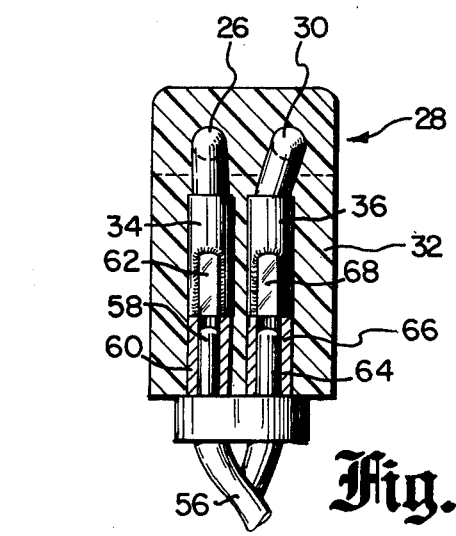
𝕱𝖎𝖌.4.
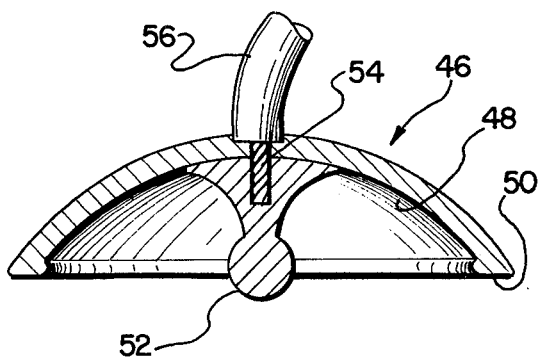
𝕱𝖎𝖌.6.
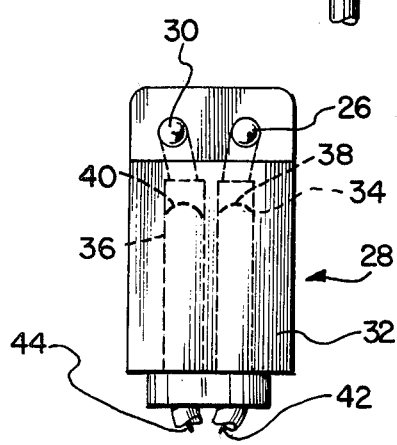
𝕱𝖎𝖌.5.

ELECTRICAL PULSE ACUPRESSURE APPARATUS AND METHOD OF MAKING SAME

BACKGROUND OF THE INVENTION

The field of this invention relates to acupressure therapy for human beings and more particularly to an improved acupressure apparatus and method of making same in which small electrical pulses are continuously transmitted to selected acupressure points to achieve treatment.

Within the human being, there are several known locations where acupuncture points, such as inside the external ear, which when subjected to acupuncture treatment, will have a therapeutic affect on corresponding body functions, reactions, muscles, organs and the like. For example, one specific acupuncture point on the ear may influence throat reaction, another the mouth function, while still another stomach activity. Location and stimulation of these sensitive acupuncture points with acupuncture therapy have been used to treat such conditions as obesity, alchololism, drug addiction, smoking, and the like.

It has been known, in the past, that it is not necessary to insert needles into the body in order to affect treatment at acupuncture points. Physical pressure applied against the acupuncture point will achieve some degree of treatment and can be as effective as the insertion of a needle. It has been known to employ the use of a molded device which is to be located within the external ear which is to exert localized pressure against one or more acupuncture points within the ear. This molded device is to be utilized by the wearer as the wearer proceeds through his or her daily routine. Therefore, the wearer is achieving continuous treatment.

The interior surface of each molded device includes one or more protruding members which are in the form of spherical nodules. Each nodule is to be located in a precise position against a certain acupuncture point. Thereby, treatment is achieved by pressure to the particular acupuncture point.

It has also been known that by not only using pressure on the acupuncture point, but also by applying pulses of electrical energy to the acupuncture point, treatment will be enhanced. These electrical pulses are at a very low current level and actually, in most instances, are not even felt by the patient. The use of these electrical pulses provide a more effective treatment in conjunction with the pressure applied to the acupuncture point.

Previously, to construct such acupressure devices, the manufacture procedure has been quite tedious. In order to transmit the pulses of electrical energies, small wires must be inserted through the molded device to connect with protruding metallic nodules which are pressing against the acupuncture points. Also, a particular type of removable electrical connector must be included within the molded device so as to connect with the wires.

SUMMARY OF THE INVENTION

The primary objective of this invention is to construct an acupressure treatment apparatus which can be manufacturered more simply and at less cost, yet functions in a satisfactory manner over an extended period of time.

The apparatus of this invention relates to devices which utilize both physical pressure against an acupuncture point and also electrical pulse treating of the acupuncture point. A molded applicator is specifically configured to be applicable to a particular human body location over an acupuncture point. The inner surface (surface directly in contact with the human body) of the molded device includes one or more protruding electrically conductive nodules. Each of the nodules connect with an interal chamber formed within the molded applicator. Within the internal chamber there is poured in liquid form an electrically conductive paste. Within the outside surface (the surface spaced fartherest from the skin surface of the user) of the applicator, there is embedded a female electrical connector within the liquid paste. As the liquid paste hardens, the metallic nodules, as well as the electrical connector, are then fixedly secured in position. The paste also functions to conduct electrical current from the electrical connector to the metallic nodules. A male plug is to be connectable to the female connector. The male plug is connected through appropriate electrical conductor assembly to a generator of electrical energy. The plug is to include an auxiliary connection so as to be connectable with a second electrical pulse acupressure apparatus.

BRIEF DESCRIPTION OF THE DRAWING

FIG. 1 is an isometric view showing the electrical pulse acupressure apparatus of this invention;

FIG. 2 is a cross-sectional view through the molded applicator taken along line 2—2 of FIG. 1, which is included within the acupressure apparatus of FIG. 1, showing the inner construction of the applicator;

FIG. 3 is a cross-sectional view of the male plug utilized in connection with the acupressure apparatus of this invention showing in detail the interior construction of the male plug;

FIG. 4 is a cross-sectional view taken along line 4—4 of FIG. 3;

FIG. 5 is an end view of the male plug taken along line 5—5 of FIG. 3; and

FIG. 6 is a cross-sectional view taken along line 6—6 of FIG. 1 showing, in more detail, the auxiliary type of acupressure apparatus shown.

DETAILED DESCRIPTION OF THE SHOWN EMBODIMENT

Referring particularly to the drawing, there is shown the acupressure apparatus 10 of this invention which incudes the use of a molded applicator 10. The molded applicator 10 will normally be constructed of plastic and is to have an exterior inner surface configuration adapted to closely conform within the configuration of a human ear. It is to be understood that each applicator 10 will be custom fitted for each particular wearer. The plastic material will normally comprise a polyethylene or a polystrene.

Formed interiorly of the applicator 10 is an internal chamber 12. Embedded within the inner surface of the applicator 10 and connector with the internal chamber 12 are a plurality of metallic nodules in the form of spherical balls 14. It is considered to be within the scope of this invention that other than metallic balls 14 could be employed. However, it is important that the nodules 14 be electrically conductive. Each of the nodules 14 fit within an appropriate hole formed within the housing 10.

Passageways, such as passageway 16, are formed within the applicator 10 and are considered to be part of the internal chamber 12. Each passageway 16 communicates with the enlarged section of the internal chamber 12.

Once the nodules 14 have been located in position, an electrically conductive paste 18 is poured into the internal chamber 12, substantially filling such. Within the outer surface of the applicator 10 and while the paste 18 is still in liquid form there is embedded a female electrical conductor 20 which has electrically conducting openings 22 and 24. A pin 26 of a male plug assembly 28 is to be inserted within opening 22. Similarly, a pin 30 of the male plug assembly 28 is to be inserted within the opening 24.

The material of construction of the paste 18 can take different forms. Copper is known to an excellent electrical conductor. An example of the desired type of paste 18 would be an epoxy compound, which contains powdered copper. The epoxy compound will function as an adhesive that, when hardened, holds into place the nodules 14 as well as the female electrical connector 20. Another desirable material for the paste 18 would be an epoxy adhesive compound which contains silver.

The pins 26 and 30 extend within appropriate openings formed within the plug housing 32, which is generally made of a plastic or other similar material. Pin 26 connects with connecting sleeve 34 which is also mounted within the plug housing 32. Similarly, the pin 30 connects with sleeve 36 which is mounted within the plug housing 32.

A pin 38 is to be extendable within the sleeve 34, with a similar pin 40 to be extendable within the sleeve 36. The pin 38 is connected to electrically conducting wire 42 and the pin 40 is electrically connected to an appropriate electrical conducting wire 44. The wires 42 and 44 are to connect with a source of electrical power, such as an electrical generator (not shown). The use of such electrical generators is deemed to be conventional and forms no specific part of this invention.

The electrical pulses from the electrical generator are to be conducted through the conductors 42 and 44, through their respective pins 38 and 40, through the respective sleeves 34 and 36 to the respective pins 26 and 30. The electrical pulses are then conducted through the openings 22 and 24 of the electrical connector, to the electrically conductive paste 18. The electrical pulses are then conducted to the nodules 14 and hence to the acupuncture points against which the nodules 14 are located.

It may be desirable to provide for the use of additional acupressure apparatus other than the molded device 10. A different type of acupressure apparatus is shown in FIGS. 1 and 6, which relates to a disc 46. The disc 46 has a concave inner surface 48 which terminates in a peripheral edge 50. Centrally mounted within the concave inner surface 48 is a metallic nodule 52. It is to be noted that the nodule 52 protrudes exteriorly of a plane which passes through the edge 50. This is so that the metallic nodule 52 will press tightly into an acupuncture point to which it is applied.

The metallic nodule 52 is connected with electrically conducting wire 54. The wire 54 is covered by a sheath 56. The outer end of the wire 54 is electrically connected to pins 58 and 64. The pin 58 is mounted within a sleeve 60, which is located within the plug housing 28. Pin 64 is mounted within sleeve 66. The sleeve 60 includes an extension 62. The extension 62 is electrically connected as by solder to the sleeve 34. Sleeve 66 includes extension 68. The extension 68 is electrically connected to sleeve 36. In this way electrical energy is tapped from the sleeves 34 and 36 through the electrical conductor 54 to the metallic nodule 52.

To secure the disc 46 to the particular location, an adhesive is placed within the concave inner surface 48. The disc 48 is then applied to a particular acupuncture point on the patient's body, which would normally be other than within the ear. The nodule 52 will press against the appropriate acupuncture point. The adhesive will hold the disc 46 in place. Normally, the disc 46 will be constructed of a material, such as a plastic.

It is to be understood that the pin 58, as well as the pins 38 and 40, can be readily disengaged from the plug housing 28. Also, the pins 26 and 30 can be readily removed from the electrical connector 20.

What is claimed is:

1. An electrical pulse acupressure apparatus adapted to be worn by a human being in contact with the ear, said apparatus comprising:

an electrical pulse applicator, said applicator to closely conform in a tight fitting manner with the interior of the ear, said applicator to be carried by the human being, metallic nodule means mounted within an exterior surface of said applicator, said applicator being adapted to receive electrical pulses from an electrical pulse generating means and conduct such through said metallic nodule means into the body of the human being, said nodule means to be located against at least one acupuncture point of the body of the human being to thereby treat a corresponding body function;

electrical connection means formed within said applicator, said applicator having an interior chamber, said electrical connection means including a hardened paste substantially completely filling said internal chamber, said metallic nodule means connecting with said hardened paste, said hardened paste being electrically conductive;

a female plug having at least one electrical connector, said female plug being embedded within said hardened paste; and a male plug assembly being electrically connected with said electrical connector of said female plug, whereby the electrical pulses from said electrical pulse generating means are conducted through said male plug and said female plug and through said hardened paste to said nodule means.

2. The apparatus as defined in claim 1 wherein:
said nodule means comprising a plurality of separate metallic nodules.

3. The apparatus as defined in claim 1 wherein:
said male plug assembly including an auxiliary electrical connection, whereby a second electrical pulse acupressure apparatus is to be capable of being electrically connected to said auxiliary electrical connection and then applied to a portion of the body of the human being exteriorly of the ear.

* * * * *